(12) United States Patent
Kaufman et al.

(10) Patent No.: US 7,776,020 B2
(45) Date of Patent: Aug. 17, 2010

(54) ABSORBENT ARTICLES HAVING AN ALIPHATIC-AROMATIC COPOLYESTER FILM

(75) Inventors: Ross Thomas Kaufman, Neenah, WI (US); Vasily Aramovich Topolkaraev, Appleton, WI (US); Gregory James Wideman, Menasha, WI (US); Richard Warren Tanzer, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 83 days.

(21) Appl. No.: 10/804,921

(22) Filed: Mar. 19, 2004

(65) Prior Publication Data

US 2005/0208294 A1  Sep. 22, 2005

(51) Int. Cl.
*A61F 13/15* (2006.01)
*A61F 13/20* (2006.01)
*B32B 5/16* (2006.01)
*B32B 5/26* (2006.01)
*B32B 27/12* (2006.01)

(52) U.S. Cl. .............. 604/385.22; 428/323; 442/393; 442/394

(58) Field of Classification Search .............. 604/370, 604/385.22; 428/304.4, 312.2, 317, 9; 442/394
See application file for complete search history.

(56) References Cited

U.S. PATENT DOCUMENTS

| | | | |
|---|---|---|---|
| 4,626,252 A | 12/1986 | Nishizawa et al. |
| 4,965,122 A | 10/1990 | Morman |
| 5,281,691 A | 1/1994 | Hubbs et al. |
| 5,292,783 A | 3/1994 | Buchanan et al. |
| 5,391,708 A | 2/1995 | Hubbs et al. |
| 5,446,079 A | 8/1995 | Buchanan et al. |
| 5,552,515 A | 9/1996 | Hubbs et al. |
| 5,559,171 A | 9/1996 | Buchanan et al. |
| 5,580,911 A | 12/1996 | Buchanan et al. |
| 5,594,068 A | 1/1997 | Buchanan et al. |
| 5,599,858 A | 2/1997 | Buchanan et al. |
| 5,611,981 A | 3/1997 | Phillips et al. |
| 5,625,029 A | 4/1997 | Hubbs et al. |
| 5,661,193 A | 8/1997 | Khemani |
| 5,676,661 A | 10/1997 | Faulks et al. |
| 5,723,159 A | 3/1998 | Phillips et al. |
| 5,733,490 A | 3/1998 | Phillips et al. |
| 5,855,798 A | 1/1999 | Phillips et al. |
| 5,900,322 A | 5/1999 | Buchanan et al. |

(Continued)

FOREIGN PATENT DOCUMENTS

EP  0993832 A1  4/2000

(Continued)

OTHER PUBLICATIONS

Supercoat Data Sheet, http://www.imerys-perfmins.com/uploadfiles/321/Supercoat.pdf.*

(Continued)

*Primary Examiner*—Melanie J Hand
(74) *Attorney, Agent, or Firm*—Armstrong Teasdale LLP

(57) ABSTRACT

An absorbent article comprising a laminated outer cover is disclosed. The laminated outer cover comprises an aliphatic-aromatic copolyester film including a filler material. The aliphatic-aromatic copolyester films have suitable breathability, vapor transfer and tensile strength properties while being substantially biodegradable.

56 Claims, 2 Drawing Sheets

U.S. PATENT DOCUMENTS

| | | | |
|---|---|---|---|
| 5,955,529 | A | 9/1999 | Imai et al. |
| 5,958,581 | A | 9/1999 | Khanarian et al. |
| 5,972,505 | A | 10/1999 | Phillips et al. |
| 5,998,505 | A | 12/1999 | Brink |
| 6,020,393 | A | 2/2000 | Khemani |
| 6,027,740 | A | 2/2000 | Puterka et al. |
| 6,096,809 | A | 8/2000 | Lorcks et al. |
| 6,103,858 | A | 8/2000 | Yamamoto et al. |
| 6,231,970 | B1 | 5/2001 | Anderson et al. |
| 6,235,815 | B1 | 5/2001 | Loercks et al. |
| 6,235,816 | B1 | 5/2001 | Lorcks et al. |
| 6,313,202 | B1 | 11/2001 | Buchanan et al. |
| 6,328,723 | B1 | 12/2001 | Burns, Jr. et al. |
| 6,342,304 | B1 | 1/2002 | Buchanan et al. |
| 6,358,604 | B1 | 3/2002 | Peiffer et al. |
| 6,368,710 | B1 | 4/2002 | Hayes |
| 6,462,120 | B2 | 10/2002 | Offerman |
| 6,485,819 | B2 | 11/2002 | Hayes |
| 6,495,656 | B1 | 12/2002 | Haile et al. |
| 6,562,938 | B2 | 5/2003 | Haile et al. |
| 6,573,340 | B1 | 6/2003 | Khemani et al. |
| 6,599,994 | B2 | 7/2003 | Shelby et al. |
| 6,617,415 | B1 | 9/2003 | Miksic et al. |
| 6,645,584 | B1 | 11/2003 | Kuusipalo et al. |
| 6,677,048 | B2 | 1/2004 | Karhuketo et al. |
| 6,686,044 | B2 * | 2/2004 | Nakai et al. ................. 428/403 |
| 6,703,115 | B2 | 3/2004 | Hale et al. |
| 6,787,245 | B1 | 9/2004 | Hayes |
| 2002/0042599 | A1 | 4/2002 | Zhao et al. |
| 2002/0098341 | A1 | 7/2002 | Schiffer et al. |
| 2002/0128344 | A1 | 9/2002 | Fujihira et al. |
| 2003/0039851 | A1* | 2/2003 | Hale et al. ................. 428/480 |
| 2003/0088033 | A1 | 5/2003 | Shelby et al. |
| 2003/0166748 | A1 | 9/2003 | Khemani et al. |
| 2003/0166779 | A1 | 9/2003 | Khemani et al. |
| 2003/0191210 | A1 | 10/2003 | Autran |
| 2003/0204027 | A1 | 10/2003 | Autran |
| 2004/0127609 | A1* | 7/2004 | Strand et al. ................. 524/115 |
| 2005/0208294 | A1 | 9/2005 | Kaufman et al. |

FOREIGN PATENT DOCUMENTS

| | | |
|---|---|---|
| EP | 1106640 A2 * | 6/2001 |
| JP | 2003-160202 | 6/2003 |
| JP | 2003-183483 | 7/2003 |
| JP | 2004-057016 | 2/2004 |
| WO | WO 9823673 A1 * | 6/1998 |
| WO | WO 01/66160 A1 | 9/2001 |
| WO | WO 02/42365 A1 | 5/2002 |
| WO | WO 0242365 A1 * | 5/2002 |
| WO | WO 02/46277 A1 | 6/2002 |
| WO | WO 2005/056656 A1 | 6/2005 |
| WO | WO 2005/056679 A1 | 6/2005 |

OTHER PUBLICATIONS

International Search Report from PCT/US2005/001266 dated Nov. 23, 3005.

Muller R-J, et al., Biodegradation of polyesters containing aromatic constituents, Journal of Biotechnology, Mar. 30, 2001, pp. 87-95, vol. 86, Elsevier Science Publishers, Amsterdam, NL.

International Search Report from PCT/US2005/000683 dated May 30, 3005.

Van Krevelen, D.W., Properties of Polymers: Their Correlation With Chemical Structure; Their Numerical Estimation And Prediction From Additive Group Contributions, 3rd Ed., 1990, pp. 16-17, 369, Elsevier, Amsterdam.

Office action from European Patent Application No. 05 705 374.6, dated Mar. 26, 2007.

"Molar Mass Distribution," http://en.wikipedia.org/w/index.php?title=Molar_mass_distrubution&printable=yes, printed Jul. 14, 2008.

Office action from European Patent Application No. 05 705 374.6, dated Jul. 22, 2008.

Official Letter issued in European Application 05 705 374.6 (Feb. 20, 2009).

* cited by examiner

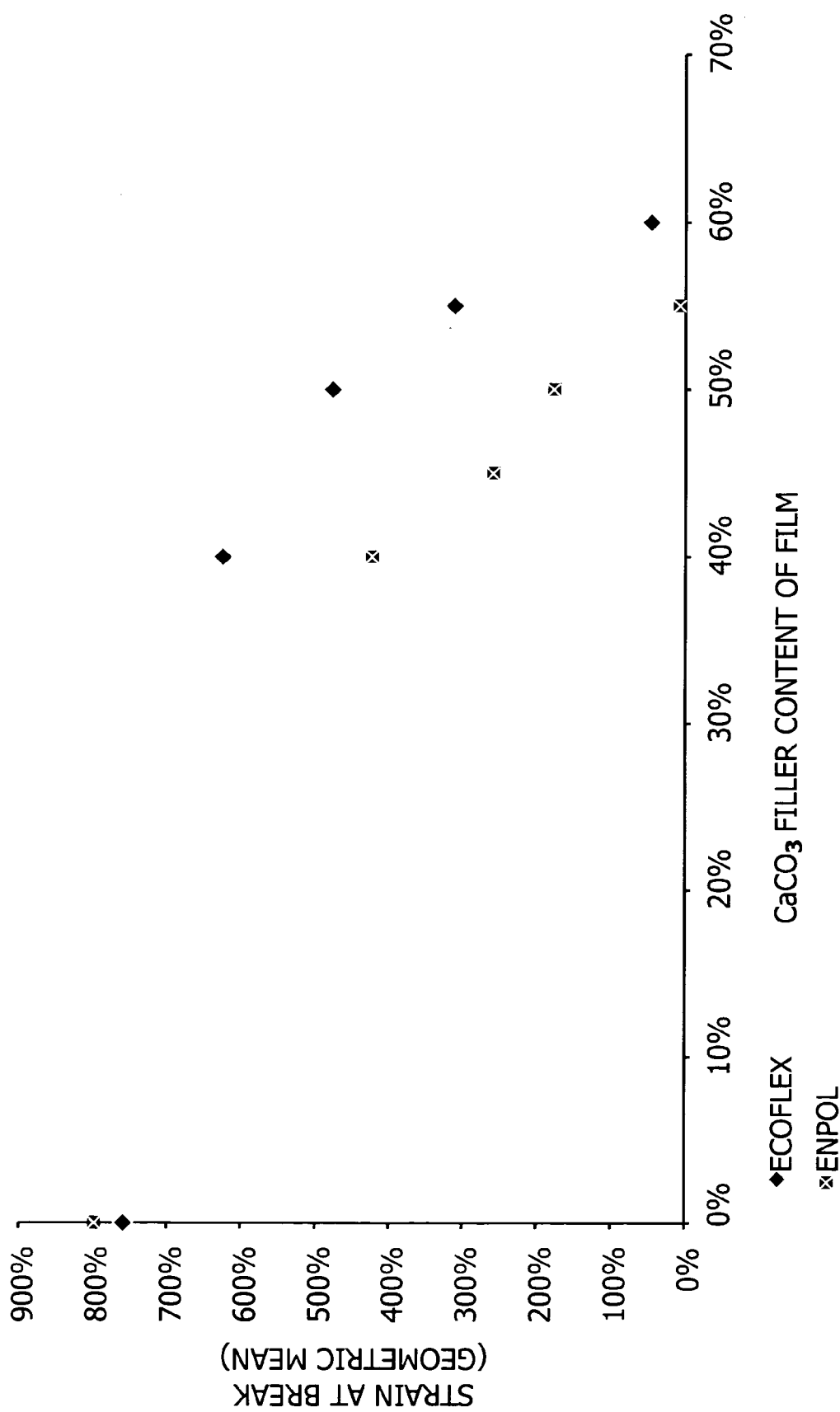

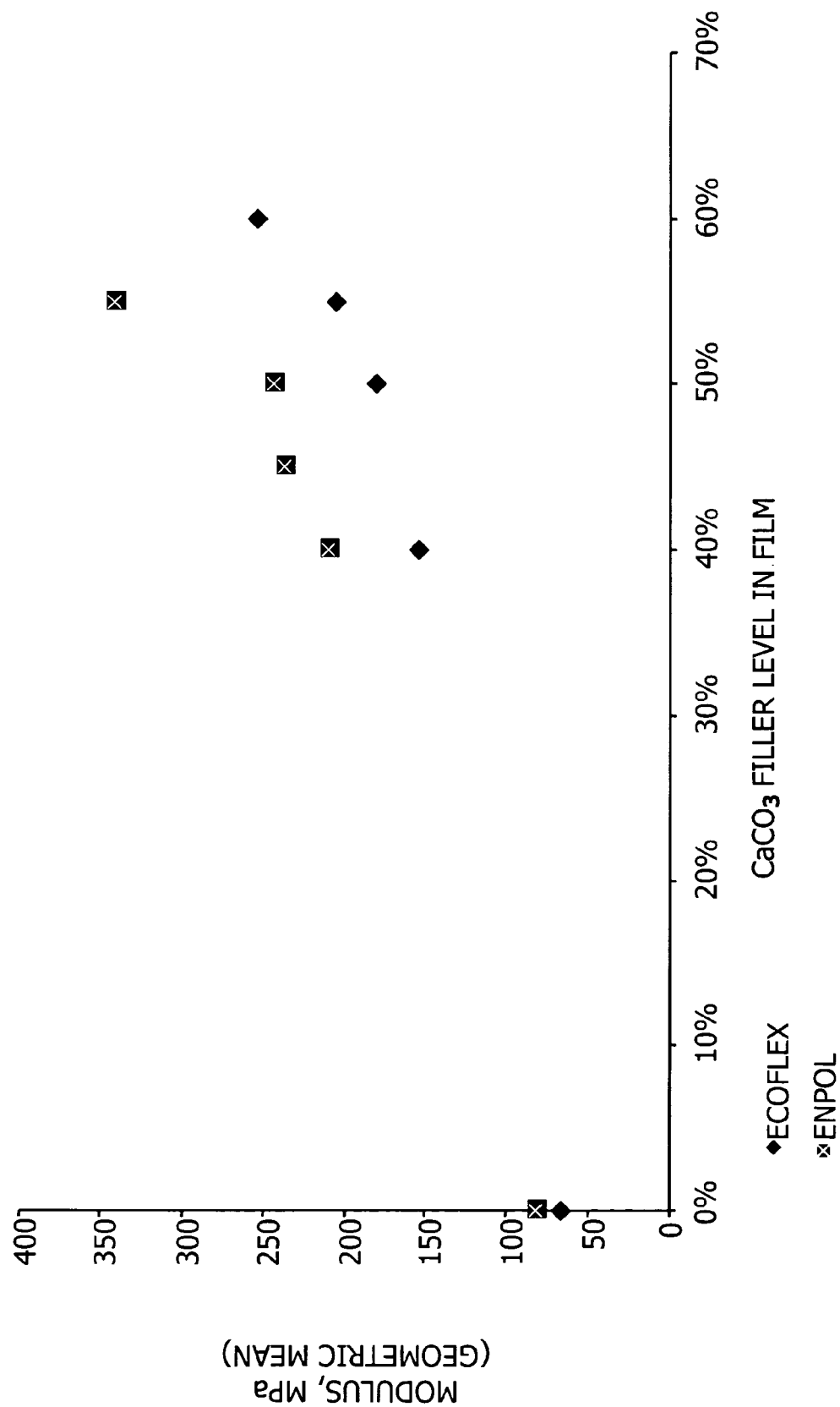

ABSORBENT ARTICLES HAVING AN ALIPHATIC-AROMATIC COPOLYESTER FILM

BACKGROUND OF THE INVENTION

The present invention is directed to absorbent articles such as diapers that contain an outer cover that comprises a substantially biodegradable film material. More particularly, the present invention is directed to absorbent articles that contain an outer cover made from a film material comprised of an aliphatic-aromatic copolyester material that shows improved biodegradability after use. When filled with a filler material such as calcium carbonate, the aliphatic-aromatic copolyester film material has high breathability and good barrier and tensile strength properties.

People rely on disposable absorbent articles, such as diapers, to make their lives easier. Diapers commercially available today are generally comfortable to the wearer, and provide a good barrier against leakage out of the diaper. Despite providing good barrier properties against liquids, many commercially available diapers allow water vapor to pass through the diaper and into the environment to lessen the amount of moisture held against the skin and reduce the chance of skin irritation and rash due to skin overhydration. In order to allow the passage of vapor through the diaper and into the environment while holding liquid, many diapers comprise a laminated outer cover, often referred to as a breathable outer cover.

Generally, this breathable outer cover is comprised of a non-woven outer-facing layer joined to an inner-facing linear low density polyethylene layer. The polyethylene layer will typically comprise calcium carbonate, which causes a series of openings to develop in the polyethylene layer when the film is stretched prior to use in the product, which ultimately allows water vapor to pass through without allowing liquid to pass through.

Although most commercially available diapers today comprise an outer cover suitable for achieving the goals outlined above, one shortcoming to date has been that the polyethylene used in the manufacturing of the diaper, and specifically one layer of the outer cover, is not substantially biodegradable. Because of the popularity of diapers and other absorbent products and the large number of these products that are utilized each year, it could be beneficial to provide absorbent article components that exhibit improved biodegradability in landfills after use and disposal.

SUMMARY OF THE INVENTION

The present invention is directed to absorbent articles or products comprising a film with improved biodegradable properties. The film, which is particularly useful as one component of an outer cover of an absorbent article, is comprised of an aliphatic-aromatic copolyester. The film also comprises calcium carbonate or other suitable filler materials such that, upon stretching, pores develop around the filler material. These pores allow for the passage of water vapor but not the passage of liquid. The film also possesses high breathability and good barrier and tensile strength properties.

In one embodiment, the film comprises filler particles and a copolyester that comprises three monomers: 1,4-butanediol, terephthalic acid, and adipic acid. The copolyester has a weight average molecular weight of from about 90,000 to about 160,000 Daltons and a number average molecular weight of from about 35,000 to about 70,000 Daltons, and comprises a total of 40 mole % to about 60 mole % of acid comonomers.

Therefore, the present invention is directed to an absorbent article comprising a laminated outer cover. The laminated outer cover comprises a biodegradable stretched aliphatic-aromatic copolyester film. The film comprises filler particles and a copolyester comprising from about 10 mole % to about 30 mole % of aromatic dicarboxylic acid or ester thereof, from about 20 mole % to about 40 mole % of aliphatic dicarboxylic acid or ester thereof, and from about 30 mole % to about 60 mole % dihydric alcohol. The weight average molecular weight of the copolyester is from about 90,000 to about 160,000 Daltons and the number average molecular weight of the copolyester is from about 35,000 to about 70,000 Daltons. The glass transition temperature of the copolyester is less than about 0° C.

The present invention is further directed to an absorbent article comprising a laminated outer cover. The laminated outer cover comprises a biodegradable stretched aliphatic-aromatic copolyester film. The film comprises filler particles and a copolyester comprising from about 10 mole % to about 30 mole % terephthalic acid, from about 20 mole % to about 40 mole % adipic acid, and from about 30 mole % to about 60 mole % 1,4-butanediol. The copolyester has a weight average molecular weight of from about 90,000 to about 160,000 Daltons and a number average molecular weight of from about 35,000 to about 70,000 Daltons. The glass transition temperature of the copolyester is less that about 0° C.

BRIEF DESCRIPTION OF THE DRAWINGS

FIG. 1 is a plot of the geometric mean of the machine direction and cross direction strain at break data against the calcium carbonate filler level of various films.

FIG. 2 is a plot of the geometric mean of the machine direction and cross direction modulus data against the calcium carbonate filler level of various films.

DETAILED DESCRIPTION OF THE PRESENTLY PREFERRED EMBODIMENTS

The present invention is generally directed to disposable absorbent products which comprise an aliphatic-aromatic copolyester film. The aliphatic-aromatic copolyester film, which in one embodiment may be utilized in combination with a spunbonded nonwoven material to form a composite outer cover, also comprises a filler material which imparts several desirable characteristics including high breathability and good barrier and tensile strength properties. Additionally, the aliphatic-aromatic copolyester films as described have improved biodegradable properties as compared to conventional film materials such as linear low density polyethylene.

Although described primarily herein in connection with a composite outer cover of an absorbent product, such as a diaper, it will be recognized by one skilled in the art based on the disclosure herein that the aliphatic-aromatic copolyester films described herein may be utilized in other areas of an absorbent article in addition to the outer cover. For example, fecal containment members, such as those described in U.S. Pat. No. 5,676,661 (Faulks et al.) may comprise the copolyester films described herein.

Additionally, although described primarily herein in connection with a diaper, it will be recognized by one skilled in the art based on the disclosure herein that the aliphatic-aromatic copolyester films described herein could also be used in a variety of other absorbent articles including, but not limited to, training pants and adult incontinence garments. Also, the aliphatic-aromatic copolyester films described herein could also be used in connection with non-absorbent articles. Suitable non-absorbent articles include, for example, surgical drapes, surgical gowns, and the like.

As used herein, the term "precursor film" is meant to include films that have not been stretched prior to use and/or evaluation and analysis. This includes films that contain a filler material, such as calcium carbonate, that have not been stretched to create the pores around the calcium carbonate to allow water vapor to pass through the film.

As used herein, the term "stretched film" is meant to include films that have been stretched to create pores around a filler material. These stretched films are ready for use in an absorbent article as they will allow water vapor to pass therethrough.

As used herein, the term "biodegradable" or "biodegradable polymer" refers to a polymer that can be readily decomposed by biological means, such as a bacterial action, environmental heat and/or moisture. When tested according to ASTM D6340-98, a biodegradable polymer is one that is at least about 80% dissolved and/or decomposed (oxidized) after 180 days in a controlled compost environment as set forth in the procedure.

Typically, the outer cover of a diaper is a multi-layered laminate or composite structure, such as a necked, multi-layer laminate structure. Such a laminated composite structure provides the desired levels of extensibility as well as liquid impermeability and vapor permeability. The laminated structure typically comprises an outward-facing layer and an inward, or bodyfacing-layer. The outward-facing layer is generally constructed of a vapor and liquid permeable non-woven material, and the inward-facing layer is generally constructed of a liquid impermeable, vapor permeable material. Such a combination allows for the transmission of vapor through the diaper and into the environment along with the holding of liquid in the diaper. The two layers are generally secured together thermally or by a suitable laminating adhesive. Thermal bonding includes continuous or discontinuous bonding using a heated roll. Point bonding is an example of such a technique. Thermal bonds should also be understood to include various ultrasonic, microwave, and other bonding methods wherein the heat is generated in the non-woven or the film.

The liquid permeable outward-facing layer can be any suitable material and is desirably one which provides a generally cloth-like texture. Suitable neckable materials for the outward-facing layer include non-woven webs, woven materials and knitted materials such as those described in U.S. Pat. No. 4,965,122 (Morman). Non-woven fabrics or webs have been formed from many processes, for example, spunbonding processes, bonded carded web processes, meltblowing processes and spunbonding spunlacing processes. Morman describes stretching a material, such as a non-woven, in one direction such that the material reversibly narrows or "necks" in the perpendicular direction. The non-elastic neckable material is desirably formed from at least one member selected from fibers and filaments of inelastic polymers. Such polymers include polyesters, for example, polylactic acid, polyhydroxy alkanoate, polyethylene terephthalate, polyolefins, for example, polyethylene and polypropylene, and polyamides, for example, nylon 6 and nylon 66 . A preferred material is a spunbond polypropylene. These fibers or filaments are used alone or in a mixture of two or more thereof. Suitable fibers for forming the neckable material include natural and synthetic fibers as well as bicomponent, multicomponent, and shaped polymer fibers.

Many polyolefins are available for fiber production including, for example, fiber forming polypropylenes including Exxon Chemical Company's Escorene PD 3445 polypropylene and Himont Chemical Company's PF-304. Polyethylenes such as Dow Chemical's ASPUN 6811A linear low density polyethylene is also a suitable polymer. The non-woven web layer may be bonded to impart a discrete bond pattern with a prescribed bond surface area. If too much bond area is present on the neckable material, it will break before it necks. If there is not enough bond area, then the neckable material will pull apart. Typically, the percent bonding area ranges from around 5 percent to around 40 percent of the area of the neckable material.

One particular example of suitable material from which the outward-facing layer may be constructed is a 0.4 osy (ounce per square yard) or 14 gsm (grams per square meter) spunbond polypropylene non-woven web which is neckable in the range of from about 35% to about 45%. Typically, a suitable nonwoven material has a basis weight of less than about 30 gsm. Also, while it is not a necessity for the outward-facing layer of the outer cover to be liquid permeable, it is desired that it have a cloth-like texture.

Another example of a suitable material from which the outward facing layer may be constructed is a polylactic acid spunbond, such as that manufactured by Unitika (Osaka Japan) or Kanebo (Tokyo, Japan).

The liquid impermeable, vapor permeable inward-facing layer is desirably constructed of a stretched aliphatic-aromatic copolyester-containing film as described herein. The aliphatic-aromatic copolyester films of the present invention comprise: (1) a copolyester that comprises an aromatic dicarboxylic acid or ester thereof, an aliphatic dicarboxylic acid or ester thereof, and a dihydric alcohol; and (2) filler particles. Optionally, a polyfunctional branching agent may also be incorporated into the aliphatic-aromatic copolyester films of the present invention.

Methods of preparing polyesters in general and aromatic-aliphatic copolyesters in particular are known in the art. Most commonly, a mixture of monomers, including an aromatic dicarboxylic acid (designated HOOC—Ar—COOH in the equation below), an aliphatic dicarboxylic acid (designated HOOC—R—COOH in the equation below), and a diol (designated HO—R'—OH in the equation below) are reacted in the presence of a catalyst. Water is driven off, and under proper conditions, a copolyester results (can be either block or random copolymers), as shown in the following equation:

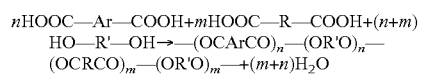

Alternative synthesis methods include using methyl esters in place of the carboxylic acids. In these methods methanol is volatilized rather than water during the reaction. Other synthesis methods are also known.

For purposes of this invention, when it is stated that a polyester comprises various monomers, it assumes that the starting materials were carboxylic acids and alcohols, as provided in the generalized equation above. While it is understood that other synthesis schemes may employ other types of monomers, reference to copolyesters comprising the stated carboxylic acids and alcohols is intended to define the finished polymer, not the actual starting materials. Also, the precise polymer synthesis method is not critical so long as the desired properties of the polymer are achieved.

Any aromatic dicarboxylic acid known in the art can be used as the aromatic dicarboxylic acid monomer of the copolyester of the films described herein. Useful aromatic dicarboxylic acids include unsubstituted and substituted aromatic dicarboxylic acids and the lower alkyl ($C_1$-$C_6$) esters of aromatic dicarboxylic acids. Examples of useful diacid moieties include those derived from terephthalates, isophthalates, naphthalates, and bibenzoates. Specific examples of useful aromatic dicarboxylic acid components include terephthalic acid, dimethyl terephthalate, isophthalic acid, dimethyl isophthalate, 2,6-napthalene dicarboxylic acid, dimethyl-2,6-naphthalate, 2,7-naphthalenedicarboxylic acid, dimethyl-2,7-naphthalate, 3,4'-diphenyl ether dicarboxylic acid, dimethyl-3,4'diphenyl ether dicarboxylate, 4,4'-diphenyl ether dicarboxylic acid, dimethyl-4,4'-diphenyl ether dicarboxylate, 3,4'-diphenyl sulfide dicarboxylic acid, dimethyl-3,4'-diphenyl sulfide dicarboxylate, 4,4'-diphenyl sulfide dicarboxylic acid, dimethyl-4,4'-diphenyl sulfide dicarboxylate, 3,4'-diphenyl sulfone dicarboxylic acid, dimethyl-3,4'-diphenyl sulfone dicarboxylate, 4,4'-diphenyl sulfone dicarboxylic acid, dimethyl-4,4'-diphenyl sulfone dicarboxylate, 3,4'-benzophenonedicarboxylic acid, dimethyl-3,4'-benzophenonedicarboxylate, 4,4'-benzophenonedicarboxylic acid, dimethyl-4,4'-benzophenonedicarboxylate, 1,4-naphthalene dicarboxylic acid, dimethyl-1,4-naphthalate, 4,4'-methylene bis(benzoic acid), dimethyl-4,4'-methylenebis(benzoate), and the like and mixtures of two or more thereof. Preferably, the aromatic dicarboxylic acid component is derived from terephthalic acid, dimethyl terephthalate, isophthalic acid, dimethyl isophthalate, 2,6-naphthalene dicarboxylic acid, dimethyl-2,6-naphthalate, or mixtures of two or more thereof. Carboxylic acid chlorides or anhydrides of these monomers may also be suitable.

The aromatic dicarboxylic acid is present in the aliphatic-aromatic copolyester in an amount of from about 10 mole % to about 30 mole %, optionally from about 15 mole % to about 25 mole %, and optionally from about 17.5 mole % to about 22.5 mole %.

Any aliphatic dicarboxylic acid known in the art can be used as the aliphatic dicarboxylic acid monomer component of the copolyester the films described herein. Useful aliphatic dicarboxylic acid components include unsubstituted, or substituted, linear, branched, or cyclic aliphatic dicarboxylic acids, and the lower alkyl esters thereof, preferably having 2-36 carbon atoms. Examples of useful aliphatic dicarboxylic acid components include, oxalic acid, dimethyl oxalate, malonic acid, dimethyl malonate, succinic acid, dimethyl succinate, methylsuccinic acid, glutaric acid, dimethyl glutarate, 2-methylglutaric acid, 3-methylglutaric acid, adipic acid, dimethyl adipate, 3-methyladipic acid, 2,2,5,5-tetramethylhexanedioic acid, pimelic acid, suberic acid, azelaic acid, dimethyl azelate, sebacic acid, 1,11-undecanedicarboxylic acid, 1,10-decanedicarboxylic acid, undecanedioic acid, 1,12-dodecanedicarboxylic acid, hexadecanedioic acid, docosanedioic acid, tetracosanedioic acid, dimer acid, 1,4-cyclohexanedicarboxylic acid, dimethyl-1,4-cyclohexanedicarboxylate, 1,3-cyclohexanedicarboxylic acid, dimethyl-1,3-cyclohexanedicarboxylate, 1,1-cyclohexanediacetic acid, and the like and mixtures of two or more thereof. Carboxylic acid chlorides or anhydrides may also be suitable. Preferred aliphatic acids or esters include succinic acid, dimethyl succinate, glutaric acid, dimethyl glutarate, adipic acid, dimethyl adipate, and dimer acid.

The aliphatic dicarboxylic acid is present in the aliphatic-aromatic copolyester in an amount of from about 20 mole % to about 40 mole %, optionally from about 25 mole % to about 35 mole %, and optionally from about 27.5 mole % to about 32.5 mole %.

Any dihydric alcohol, glycol, or diol known in the art can be used as the dihydric alcohol component of the aliphatic-aromatic copolyester of the film of the present invention. Examples include unsubstituted or substituted; straight chain, branched, cyclic aliphatic, aliphatic-aromatic, or aromatic diols having e.g., from 2 carbon atoms to 36 carbon atoms and poly(alkylene ether) diols with molecular weights preferably between about 250 to about 4,000. Specific examples of the useful diol component include ethylene glycol, 1,3-propanediol, 1,4-butanediol, 1,6-hexanediol, 1,8-octanediol, 1,10-decanediol, 1,12-dodecanediol, 1,14-tetradecanediol, 1,16-hexadecanediol, 4,8-bis(hydroxymethyl)-tricyclo [5.2.1.0/2.6]decane, 1,4-cyclohexanedimethanol, di(ethylene glycol), tri(ethylene glycol), poly(ethylene oxide) glycols, poly(butylene ether) glycols, isosorbide, and the like and mixtures of two or more. Preferred dihydric alcohols include ethylene glycol, 1,3-propanediol, 1,4-butanediol, 1,6-hexanediol, and poly(ethylene oxide) glycols.

The dihydric alcohol is present in the aliphatic-aromatic copolyester in an amount of from about 30 mole % to about 60 mole %, optionally from about 45 mole % to about 55 mole %, and optionally from about 47.5 mole % to about 52.5 mole %.

The aliphatic-aromatic copolyester component of the films described herein may be formed including an optional polyfunctional branching agent, such as any material with three or more carboxylic acid functions, hydroxy functions or a mixture thereof. Specific examples of useful polyfunctional branching agent component include 1,2,4-benzenetricarboxylic acid (trimellitic acid), trimethyl-1,2,4-benzenetricarboxylate, 11,2,4-benzenetricarboxylic anhydride (trimellitic anhydride), 1,3,5-benzenetricarboxylic acid, 1,2,4,5-benzenetetracarboxylic acid (pyromellitic acid), 1,2,4,5-benzenetetracarboxylic dianhydride (pyromellitic anhydride), 3,3',4,4'-benzophenonetetracarboxylic dianhydride, 1,4,5,8-naphthalenetetracarboxylic dianhydride, citric acid, tetrahydrofuran-2,3,4,5-tetracarboxylic acid, 1,3,5-cyclohexanetricarboxylic acid, pentaerythritol, 2-(hydroxymethyl)-1,3-propanediol, 2,2-bis(hydroxymethyl)propionic acid, and the like and mixtures of two or more thereof. The polyfunctional branching agent may be included when higher resin melt viscosity is desired for specific end uses. Excessive fractions of polyfunctional groups (i.e., more than two functional groups) may lead to the formation of a gel fraction or insoluble crosslinked material. The total amount of polyfunctional branching agent may be less than about 10% of the total monomer composition. Alternatively the polyfunctional branching agent may be less than about 3%, or less than about 1%.

In one embodiment of the present invention, the total amount of acid comononer present in the aliphatic-aromatic copolyester component of the films described herein is from about 40 mole % to about 60 mole %; that is, the molar amount of aromatic dicarboxylic acid plus the molar amount of aliphatic dicarboxylic acid present in the aliphatic aromatic copolyester is from about 40 mole % to about 60 mole %. Desirably, the total amount of acid comonomer present in the copolyester is from about 45 mole % to about 55 mole %, and even more desirably from about 47.5 mole % to about 52.5 mole %.

The total amount of acid comonomer present in the aliphatic-aromatic copolyester component of the films described herein affects the adhesion properties between the aliphatic-aromatic copolyester and the filler material component of the film, which is described below. In order for films to be suitable for use in absorbent products, generally low adhesion between the filler material and the copolyester is desired. If too much acid comonomer is present in the copolyester, the adhesion to the filler material is too high. And the filler material cannot act properly to effectuate the creation of pores around the filler material when the film is stretched. This results in the film having insufficient vapor permeability.

The aliphatic-aromatic copolyester component of the films described herein have a weight average molecular weight and a number average molecular weight such that the copolyester has a suitable tensile strength. If the molecular weight numbers are too small, the copolyester will be too tacky and have too low of a tensile strength. If the molecular weight numbers are too high, various processing issues, such as a need for increased temperature to deal with increased viscosity, are encountered. Suitable weight average molecular weights for the copolyesters are from about 90,000 to about 160,000 Daltons, desirably from about 100,000 to about 130,000 Daltons, and more desirably from about 105,000 to about 120,000 Daltons. Suitable number average molecular weights for the copolyesters are from about 35,000 to about 70,000 Daltons, more desirably from about 40,000 to about 60,000 Daltons, and more desirably from about 42,000 to about 50,000 Daltons.

The aliphatic-aromatic copolyester films of the present invention generally have a thickness suitable for use in an absorbent article, such as a diaper. Typically, the films will have a thickness of less than about 250 micrometers, and desirably from about 2.5 micrometers to about 130 micrometers. A standard film useful in a diaper may have a thickness of from about 10 micrometers to about 25 micrometers, for example. In some embodiments, it may be desirable to utilize a film having a thickness of about 50 micrometers.

The copolyesters described herein for use in the films of the present invention have a glass transition temperature such that the copolyester has suitable flexibility characteristics for use in a film. As used herein, "glass transition temperature" means that temperature at which a polymer becomes hard and brittle, like glass. For the copolyesters described herein, it is desirable that they have a glass transition temperature of less than about 0° C., and optionally less than about −10° C. With glass transition temperatures less than these values, the copolyesters have suitable properties for use in the absorbent articles described herein.

The aliphatic-aromatic copolyester films of the present invention have a suitable water vapor transmission rate such that the film allows a substantial amount of water vapor to pass therethrough such that the probability of skin overhydration is reduced. The films of the present invention can be made substantially vapor permeable through the addition of a filler particle or material during manufacturing of the films. During manufacturing, the filler material is admixed with the polymers prior to the casting of the polymers into a film. Once casted, the films are stretched to create tiny pores to form in the film around the filler particles. These pores allow vapor transmission, but do not allow a substantial amount of liquid to pass therethrough.

The filler particles can include any suitable inorganic or organic filler. The filler particles are preferably small, in order to maximize vapor transmission through the voids. Generally, the filler particles should have a mean particle diameter of about 0.1-10.0 micrometers, optionally about 0.5-5.0 micrometers, and optionally about 1.5-3.0 micrometers. Examples of organic fillers include starches, such as thermoplastic starches or pregelatinized starches, microcrystalline cellulose, and polymeric microbeads. Other Suitable fillers include, without limitation, calcium carbonate, non-swellable clays, silica, alumina, barium sulfate, sodium carbonate, talc, magnesium sulfate, titanium dioxide, zeolites, aluminum sulfate, diatomaceous earth, magnesium sulfate, magnesium carbonate, barium carbonate, kaolin, mica, carbon, calcium oxide, magnesium oxide, aluminum hydroxide and polymer particles. Calcium carbonate is a presently preferred filler material.

The filler particles may optionally be coated with a minor quantity (e.g. up to 2% by weight) of a fatty acid or other material to ease their dispersion in the polymer matrix prior to casting. Suitable fatty acids include without limitation stearic acid, or a larger chain fatty acid such as behenic acid. The amount of filler particles in the film should range from about 30% to about 80% (by weight film and filler particles), optionally from about 40% to about 70% (by weight of film and filler particles), and optionally from about 50% to about 65% (by weight film and filler particles), and optionally from about 50% to about 55% (by weight of film and filler particles).

Filler particles may be microporous or not. Microporous refers to a material that has pores, generally in the range of from about 2 Angstroms to about 50 Angstroms, that form a continuously interconnecting void space or network. The shape of the filler particle may be generally spherical or rounded. Other embodiments include plate-like, needle-like, or irregular shapes, points, or sharp edges.

In some embodiments of the present invention, the stretched films described herein have a water vapor transmission rate of at least about 2000 g/m$^2$/day, optionally at least about 5000 g/m$^2$/day, optionally at least about 10,000 g/m$^2$/day, and optionally 25,000 g/m$^2$/day. At these levels, the films allow a sufficient amount of water vapor to pass through to protect the skin from overhydration.

In addition to a suitable water vapor transmission rate, it is also desirable that the stretched films described herein resist a hydrostatic pressure such that the films do not allow a substantial amount of liquid water to pass through upon the application of pressure. Generally, it is desirable that the films resist a hydrostatic pressure of at least about 60 millibar, optionally at least about 80 millibar, optionally at least about 120 millibar, and optionally at least about 180 millibar without allowing liquid water to pass.

In addition to a suitable water vapor transmission rate and a suitable resistance to hydrostatic pressure, it is also desirable that the films described herein have a suitable modulus of elasticity. The tensile properties of the films disclosed herein can be determined by one skilled in the art using the "Standard Test Method For Tensile Properties of Plastics" ASTM D 938-99, published by the American Society for Testing and Materials, West Conshohocken, Pa. The procedure indicates that break stress is the tensile stress at the break elongation (i.e., the elongation at which the sample breaks); yield stress is the tensile stress at the first point on the stress-strain curve at which an increase in strain occurs without an increase stress; and modulus of elasticity is the ratio of stress (nominal) to corresponding strain below the proportional limit of a material.

Precursor films desirably have a modulus of elasticity ratio which is suitable to characterize a desirable adhesion between filler particles and the film. As used herein, the term "modulus ratio" means the modulus of elasticity of a filled precursor film divided by the modulus of elasticity of an unfilled film. For precursor films comprising about 50% filler material, the modulus ratio is desirably from about 0.5 to about 3.5, optionally from about 0.75 to about 3.25, and optionally from about 1.0 to about 3.0. For precursor films comprising about 55% filler material, the modulus ratio is from about 0.45 to about 4.25, optionally from about 0.75 to about 3.75, and optionally from about 1.0 to about 3.5. Within these ratios, a film has the desired modulus of elasticity to provide a desired rate of adhesion between the film and the filler particles.

Additionally, precursor films desirably have suitable elongation characteristics; that is, the precursor film can be elongated a sufficient amount to achieve the desired film thickness and level of breathability before breaking. Measurements of elongation of a film include % strain at break point, break stress (MPa) and yield stress (MPa). For precursor films comprising about 50% filler material, it is desirable that the film can be stretched in the machine direction and have from about 50% strain to about 1000% strain, optionally from about 300% strain to about 1000% strain, and optionally from about 450% strain to about 1000% strain before breaking. As used herein, "strain" means the ratio of the length of the stretched film to the length of the precursor film minus one, which is typically reported as a percentage.

For precursor films comprising about 55% filler material, it is desirable that the film can be stretched in the machine direction and have from about 50% strain to about 1000% strain, optionally from about 75% strain to about 1000% strain, and optionally from about 250% strain to about 1000% strain before breaking.

It is also beneficial for the precursor films to have a suitable draw ratio in the machine direction. As used herein, "draw ratio" means the length of stretched film divided by the length of unstretched film. In one embodiment, the draw ratio of the precursor films described herein is at least about 2.5 to about 10, optionally from about 3.5 to about 10, and optionally from about 4.5 to about 10.

For precursor films comprising about 50% filler material, it is desirable that the film can be stretched in the cross direction and not break until from about 50% strain to about 1000% strain, optionally from about 300% strain to about 1000% strain, and optionally from about 450% strain to about 1000% strain before breaking. For precursor films comprising about 55% filler material, it is desirable that the film can be stretched in the cross direction and not break until from about 50% strain to about 1000% strain, optionally from about 250 strain to about 1000% strain, and optionally from about 350% strain to about 1000% strain before breaking.

For precursor films comprising about 50-55% filler material, it is desirable that the film can be stretched in the machine direction and have a break stress of from about 4 to about 30 MPa, optionally from about 6 to about 20 MPa, and optionally from about 8 to about 15 MPa. For precursor films comprising from about 50 to about 55% filler material, it is also desirable that the film can be stretched in the machine direction and have a yield stress of from about 4 to about 16 MPa, optionally from about 6 to about 14 MPa, and optionally from about 8 to about 10 MPa. As one skilled in the art will understand based on the disclosure herein, the films described herein can be stretched by any method known in the art. For example, the films can be stretched by blowing, using tenter hooks, or by using differential speeds on rollers.

For stretched films, it is preferred that the film have a modulus of elasticity of from about 50 to about 250 MPa, optionally from about 70 to about 150 MPa, and optionally from about 80 to about 100 MPa. Regarding elongation, it is preferred that stretched films be capable of being elongated in the machine direction from about 15 to about 100% strain, optionally from about 20 to about 60% strain, and optionally from about 30 to about 50% strain before breaking. Stretched films are also desirably capable of being stretched in the cross direction from about 150 to about 500% strain, optionally from about 175 to about 400% strain, and optionally from about 200 to about 300% strain before breaking. Also, when being stretched in the machine direction, stretched films desirably have a break stress of from about 10 to about 50 MPa, optionally from about 15 to about 40 MPa, and optionally from about 25 to about 35 MPa.

As noted above, the aliphatic aromatic copolyesters described herein can be prepared from the aliphatic dicarboxylic acid, aromatic dicarboxylic acid, and dihydric acid monomers using any conventional process known to those skilled in the art. For example, the copolyesters may be prepared using a conventional polycondensation technique, or a conventional melt polymerization method. Additionally, aliphatic-aromatic copolyesters may be obtained commercially from BASF (Mount Olive, N.J.), IRe Chemical (Seoul, Korea) and Eastman Chemical (Kingsport, Tenn.).

Films comprising the copolyesters and filler particles described herein and suitable for use in the absorbent articles described herein may be prepared utilizing any conventional film forming technique including extrusion casting and melt blowing. An extrusion casting technique may be used in combination with film annealing, film stretching, and/or heat setting after stretch operations.

In one embodiment, during the film casting operation, cast rolls are optionally set at the temperature at the roll surface of from about 20° C. to about 70° C., optionally from about 30° C. to about 60° C. and optionally from about 45° C. to about 55° C. After the film is cast on a cast roll, the film may be cooled and annealed at temperatures ranging from about 40° C. to about 60° C. This cooling and annealing occurs as the film is conveyed (on a series of rollers, on a conveyer belt, on an air conveyer etc.) under low tension. In this context, "low tension" indicates that the film stretches less than 100%, optionally less than 25%, or less than 10% as it is conveyed. This section of the film-making apparatus extending from the cast roll to the stretching operation is referred to as the casting line.

The casting line length is from about 5 meters to about 50 meters, optionally from about 10 meters to about 30 meters. Longer line length may provide longer residence time for film setting and annealing before film enters stretching operation. Longer residence time will improve film tensile properties such as strength, drawability, and other properties useful for stretching operations.

In a stretching operation, film is preferably stretched at temperatures from about 15° C. to about 50° C., optionally from about 25° C. to about 40° C., and optionally from about 30° C. to about 40° C. Cold stretching could improve void formation around filler particles, but may limit film stretchability. Optionally, film is stretched in two zones with optional heating to a range of from about 30° C. to about 50° C. between stretching zones. Either a single stretch or zone or multiple zones may be used. Films can be stretched uniaxially, biaxially or both uniaxially and biaxially (at different times). Uniaxial stretching may be in the machine direction, the cross direction, or on a bias.

The stretch or draw ratio during stretching operation is from about 2.5 to about 10; e.g., the linear speed of the film exiting the stretching operation is 2.5 to 10 times the speed of the precursor film entering the stretching operation. Optionally, the stretch or draw ratio is from about 3.5 to about 7.

After stretching, the film is optionally heat-set to stabilize the stretched film. Heat-setting can be accomplished at temperatures of from about 40° C. to about 80° C., and optionally from about 50° C. to about 70° C. The heat-setting operation could reduce shrinkage of the stretched film and improve film properties and breathability. Any known in the art techniques for heat setting could be used including heated rolls and oven setting. Additional treatments may be applied to improve stretched film properties such as surface treatments, UV treatments, ultrasonic treatments, and plasma treatments.

EXAMPLE 1

In this Example, aliphatic-aromatic copolyester films were prepared using two commercially available aliphatic-aromatic copolyester resins as starting materials. One group of films was prepared without any filler material, and a second group of films was prepared using a calcium carbonate filler materials at various levels (weight % of filler based on total weight of film and filler). One group of filled and unfilled films was prepared using Ecoflex F BX 7011 aliphatic-aromatic copolyester (BASF), and one group of films was prepared using EnPol G8060M (IRe Chemical) aliphatic-aromatic copolyester.

Before extrusion of the films from the aliphatic-aromatic copolyesters, the one group of Ecoflex copolyesters and one group of EnPol copolyesters were separately blended with Omya (Proctor, Vt.) 2sst 2 micron calcium carbonate filler material using a Werner & Pfleiderer (Ramsey, N.J.) ZSK-30 twin screw compounding extruder. Blends of the calcium carbonate filler material and each resin (in molten form) were made at levels of filler equal to 40 weight % (based on the total weight of the film and the filler), 50 wt %, 55 wt %, 60 wt %, and 65 wt %.

After the resins were blended with the filler material, films of each blend were extruded. The films were extruded using a HAAKE (Thermo Electron Corporation, Woburn, Mass.) Rheocord 90 benchtop twin screw extruder having an eight inch die. The extruder had three temperature zones, a melt pump with controlled temperature, and a die with a controlled temperature. Unfilled films comprising each copolyester were also extruded.

The temperature profile used for casting the Ecoflex copolyester into a film was as follows: 160° C., 170° C., 170° C. (extruder temperatures), 170° C. (melt pump temperature), and 160° C. (die temperature). The temperature profile used for casting the EnPol copolyester into a film was as follows: 170° C., 180° C., 180° C. (extruder temperatures), 180° C. (melt pump temperature), and 180° C. (die temperature). The temperature profiles were selected to achieve the proper viscosity for handling of the molten polymer. Both filled and unfilled films having a thickness ranging from about 15 micrometers to about 50 micrometers were extruded.

EXAMPLE 2

In this Example, tensile strength testing was performed on various aliphatic-aromatic copolyester precursor films prepared in Example 1. Each film to be tested was cut into a 3 millimeter wide by 50 millimeter long film strip for testing. The tensile testing was done pursuant to ADTM D-638 using a dog bone configuration, 0.7 inch (18 millimeter) gauge length, and a cross head speed of 5 inches (127 millimeters) per minute. The films were stretched under these conditions until they broke.

The following Exoflex-based and EnPol-based films were stretched and tested in the machine direction and in the cross direction: (1) 0% calcium carbonate at 25 micrometers; (2) 40% calcium carbonate at 50 micrometers; (3) 50% calcium carbonate at 50 micrometers; (4) 55% calcium carbonate at 50 micrometers; (5) 60% calcium carbonate at 50 micrometers. Also, linear low density polyethylene was tested for comparison purposes. The results are set forth in Tables 1-5.

TABLE 1

Tensile Strength Properties Of Linear Low Density Polyethylene Films

| | LLPDE | |
|---|---|---|
| | Machine Direction | Cross Machine Direction |
| Thickness (micrometers) | 25 | 25 |
| % Strain @ Break | 700 | 747 |
| Peak Stress (MPa) | 31 | 31 |
| Stress @ Yield (MPa) | 8 | 9 |
| Modulus (MPa) | 102 | 105 |

TABLE 2

Machine Direction Tensile Properties of Copolyester Precursor Films

| | Ecoflex No Fill MD | Ecoflex/ CaCO$_3$ 60/40 MD | Ecoflex/ CaCO$_3$ 50/50 MD | Ecoflex/ CaCO$_3$ 45/55 MD | Ecoflex/CaCO$_3$ 40/60 MD |
|---|---|---|---|---|---|
| Thickness (micrometers) | 25 | 50 | 50 | 50 | 50 |
| % Strain @ Break | 609 | 561 | 470 | 259 | 48 |
| Peak Stress (MPa) | 36 | 18 | 11 | 9 | 12 |
| Stress @ Yield (MPa) | 8 | 8 | 9 | 9 | 12 |
| Modulus (MPa) | 60 | 153 | 177 | 192 | 277 |

TABLE 3

Cross Machine Direction Tensile Properties of Precursor Films

| | Ecoflex No Fill CD | Ecoflex/ CaCO$_3$ 60/40 CD | Ecoflex/ CaCO$_3$ 50/50 CD | Ecoflex/CaCO$_3$ 45/55 CD | Ecoflex/ CaCO$_3$ 40/60 CD |
|---|---|---|---|---|---|
| Thickness (micrometers) | 25 | 50 | 50 | 50 | 50 |
| % Strain @ Break | 945 | 696 | 484 | 374 | 45 |
| Peak Stress (MPa) | 40 | 16 | 10 | 8 | 10 |
| Stress @ Yield (MPa) | 9 | 8 | 9 | 8 | 10 |
| Modulus (MPa) | 72 | 155 | 183 | 219 | 233 |

TABLE 4

Machine Direction Tensile Properties of Copolyester Precursor Films

| | EnPol No Fill MD | EnPol/ CaCO$_3$ 60/40 MD | EnPol/ CaCO$_3$ 55/45 MD | EnPol/ CaCO$_3$ 50/50 MD | EnPol/ CaCO$_3$ 45/55 MD |
|---|---|---|---|---|---|
| Thickness (micrometers) | 25 | 50 | 50 | 50 | 50 |
| % Strain @ Break | 715 | 378 | 330 | 231 | 8 |
| Peak Stress (MPa) | 32 | 17 | 13 | 12 | 14 |
| Stress @ yield (MPa) | 7 | 11 | 13 | 12 | 14 |
| Modulus (MPa) | 78 | 210 | 237 | 227 | 352 |

TABLE 5

Cross Machine Direction Tensile Properties of Precursor Films

|  | EnPol No Fill CD | EnPol/ CaCO₃ 60/40 CD | EnPol/ CaCO₃ 50/50 CD | EnPol/ CaCO₃ 45/55 CD | EnPol/ CaCO₃ 40/60 CD |
| --- | --- | --- | --- | --- | --- |
| Thickness (micrometers) | 25 | 50 | 50 | 50 | 50 |
| % Strain @ Break | 889 | 474 | 203 | 136 | 7 |
| Peak Stress (MPa) | 36 | 14 | 12 | 11 | 12 |
| Stress @ Yield (MPa) | 14 | 11 | 12 | 11 | 12 |
| Modulus (MPa) | 86 | 210 | 237 | 262 | 332 |

FIGS. 1 and 2 are derived from the data in Tables 2-5. FIG. 1 plots the geometric mean of the MD and CD strain at break data against the calcium carbonate filler level. FIG. 2 plots the geometric mean of the MD and CD modulus data against the calcium carbonate filler level. Geometric mean is calculated by taking the square root of the product of the machine direction data times the cross machine direction data.

The data in Tables 2-5 and in FIGS. 1 and 2 show that the strain at break for unfilled (i.e., 0% calcium carbonate) Exoflex and EnPol are quite close. Also the unfilled films have similar modulus. But as the filler level increases, the values for the Ecoflex and EnPol films diverge. Considering the films containing 40% or more filler, the EnPol-based films are stiffer than the Ecoflex-based films as shown by the higher modulus and lower strain at break for the EnPol-based films relative to the Ecoflex-based films. These differences indicate that the filler particles adhere to the EnPol-based films more strongly than the filler particles adhere to the Ecoflex-based films.

It is desirable that the filler particles do not adhere too strongly to the copolyesters. Weaker adhesion permits more stretching of the film without breakage. Also, weaker adhesion results in more debonding (separation) of the filler particles from the polymer when the film is stretched. Such separation provides voids in the film, which enhances vapor permeability. These voids also tend to result in a lower density film.

EXAMPLE 3

In this Example, various Ecoflex-based and EnPol-based precursor films extruded in Example 1 were stretched to produce stretched films to create pores around the calcium carbonate filler material such that the films could be further evaluated for hydrohead pressure, water vapor transmission rate, and tensile strength. The films were stretched to create the pores prior to further analysis in order to test the films as they would be used in a commercial embodiment; that is, the filled films extruded in Example 1 would first be stretched according to the procedure in this Example prior to being used in an absorbent article as this stretching creates the pores in the film that allow for vapor transmission.

Each film was cut into sheets measuring about 18.0 centimeters wide by about 10.0 centimeters long. Each film was then stretched to about 470% (strain) of its original length at a rate of 840 millimeters/minute, which resulted in a stretch of 2200%/minute and a draw of 350%. All Ecoflex films were successfully stretched up to a concentration of 60% calcium carbonate. The EnPol films could not be successfully stretched to the same extent with more than a concentration of 40% calcium carbonate because the film broke at higher calcium carbonate loading levels. It is hypothesized that excessive adhesion of the copolyester to the filler particles resulted in the EnPol film's lesser tolerance for stretching than the Ecoflex films.

To account for the adhesion differences between the two films, analytical work (gel permeation chromatography for molecular weight determination) was performed on the Ecoflex and EnPol copolyesters. It was determined that the EnPol resins had a higher weight average molecular weight (119,300 Daltons) as compared to the Ecoflex resins (109,850 Daltons). The EnPol resin also had a lower number average molecular weight (43,800 Daltons) as compared to the Ecoflex resin (46,700 Daltons). It was also determined that the EnPol resin had a higher total amount of acid monomer content (57 mole %) as compared to Ecoflex (51 mole %). It appears that the combination of molecular weight differences and difference in total acid monomer content caused the EnPol films to have an increased amount of tackiness which does not allow for as much debonding as compared to the Ecoflex films.

EXAMPLE 4

In this Example, the resistance to hydrostatic pressure of various films stretched according to Example 3 were evaluated. The resistance of a material to liquid penetration is measured by hydrostatic pressure. The resistance to hydrostatic pressure of various films were determined using ASTM Standard Test Method for Coated Fabrics, designation D751, "Hydrostatic Resistance Procedure A-Mullen Type Tester" with the exception that in paragraph 40.1.1, the dial reading is taken when the third drop of water is observed, rather than when the first drop is observed. All films were stretched in the machine direction.

The following Ecoflex comprising films, stretched according to Example 3, were evaluated: Exoflex with 55% calcium carbonate (25 micrometers); Exoflex with 50% calcium carbonate (25 micrometers); and Ecoflex with 40% calcium carbonate (20 micrometers). The following EnPol comprising film, also stretched according to Example 3, was evaluated: EnPol with 40% calcium carbonate (23 micrometers). The results of the hydrostatic pressure analysis are shown in Table 6.

TABLE 6

| | | Hydrohead Pressure | | |
| --- | --- | --- | --- | --- |
| Base Resin | % CaCO₃ | Thickness (micrometers) | Stretch Direction | Pressure at Failure (Mbar) |
| Ecoflex | 55 | 25 | MD | 100 |
| Ecoflex | 50 | 25 | MD | 100 |
| Ecoflex | 40 | 20 | MD | 148 |
| EnPol | 40 | 23 | MD | 104 |

As the data in Table 6 indicate, all of the films tested had high hydrohead pressure resistance values, which indicates that all of the films would be resistant to allowing water droplets to pass therethrough during use. Notably, the Ecoflex comprising 40% calcium carbonate (20 micrometers) had a value of 148.00, which indicates that it would be highly resistant to the passage of liquid therethrough.

EXAMPLE 5

In this Example, the water vapor transmission rates of various films stretched according to Example 3 were evaluated. Water vapor transmission rate measures the ability of water vapor to penetrate through a film. The water vapor transmission rate of various films were determined using ASTM F-1249 using a Permatran 100 K analyzer available from MOCON (Minneapolis, Minn.). Films were either stretched in the machine direction or the cross direction as noted below.

The following Ecoflex comprising films were evaluated: Exoflex with 55% calcium carbonate (19 micrometers machine direction); Exoflex with 55% calcium carbonate (25 micrometers machine direction); Ecoflex with 55% calcium carbonate (25 micrometers cross direction); Ecoflex with 50% calcium carbonate (23 micrometers machine direction); Ecoflex with 50% calcium carbonate (19 micrometers machine direction); Ecoflex with 40% calcium carbonate (17 micrometers machine direction); and Ecoflex with 40% calcium carbonate (22 micrometers machine direction). The following EnPol comprising films were evaluated: EnPol with 40% calcium carbonate (18 micrometers machine direction); EnPol with 40% calcium carbonate (20 micrometers cross direction); EnPol with 40% calcium carbonate (15 micrometers cross direction); EnPol with 40% calcium carbonate (25 micrometers machine direction; and EnPol with 40% calcium carbonate (20 micrometers machine direction). The results of the water vapor transmission rate analysis are shown in Table 7.

All Ecoflex films were prepared from resins having a temperature as they came out of the die during casting of about 175° C. The EnPol tested at 40% calcium carbonate were cast at about 160° C.

TABLE 7

Water Vapor Transmission Rate

| Base Resin | % CaCO$_3$ | Thickness (micrometers) | Stretch Direction | g/m$^2$/day |
|---|---|---|---|---|
| Ecoflex | 55 | 19 | MD | 21,207 |
| Ecoflex | 55 | 25 | MD | 19,763 |
| Ecoflex | 55 | 25 | CD | 16,405 |
| Ecoflex | 50 | 23 | MD | 15.660 |
| Ecoflex | 50 | 19 | MD | 13,995 |
| Ecoflex | 40 | 17 | MD | 3498 |
| Ecoflex | 40 | 22 | MD | 3091 |
| EnPol | 40 | 18 | MD | 3371 |
| EnPol | 40 | 20 | CD | 2918 |
| EnPol | 40 | 15 | CD | 2593 |
| EnPol | 40 | 23 | MD | 2348 |
| EnPol | 40 | 20 | MD | 2322 |

The data in Table 7 demonstrate that films with higher filler loading levels tend to have greater water vapor transmission rates than films with lower filler loading.

EXAMPLE 6

In this Example, the tensile strengths of various stretched films prepared according to Example 3, were evaluated for modulus, % strain at break, peak stress, and peak load using the same testing procedure as set forth in Example 2. The films were stretched in the machine direction (Table 8) and in the cross machine direction (Table 9). The results are set forth in Tables 8 and 9.

TABLE 8

Tensile Properties of Stretched Breathable Films; Films MD Stretched and MD Tested

| | LLPDE MD | EnPol/CaCO$_3$ 60/40 MD Stretched MD | Ecoflex CaCO$_3$ 45/55 MD Stretched MD |
|---|---|---|---|
| Thickness (micrometers) | 23 | 23 | 25 |
| % Strain @ break | 72 | 47 | 35 |
| Peak Stress (MPa) | 34 | 41 | 33 |
| Peak Load (gf) | 234 | 287 | 253 |
| Modulus (MPa) | 322 | 125 | 85 |

TABLE 9

Tensile Properties of Stretched Breathable Films; Films MD Stretched and CD Tested

| | LLPDE CD | EnPol/CaCO$_3$ 60/40 MD Stretched CD | Ecoflex CaCO$_3$ 45/55 MD Stretched CD |
|---|---|---|---|
| Thickness (micrometers) | 23 | 23 | 25 |
| % Strain @ break | 187 | 460 | 222 |
| Peak Stress (MPa) | 3 | 4 | 2 |
| Peak Load (gf) | 21 | 28 | 14 |
| Modulus (MPa) | 73 | 88 | 12 |

As the data in these Tables indicate, both the EnPol and Ecoflex-based films have similar properties to LLPDE once stretched.

It will be appreciated that details of the foregoing embodiments, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

What is claimed is:

1. An absorbent article comprising a laminated outer cover, the laminated outer cover comprising a biodegradable stretched aliphatic-aromatic copolyester film, the film comprising filler particles, a polyfunctional branching agent, and a copolyester comprising from about 10 mole % to about 30 mole % of aromatic dicarboxylic acid or ester thereof, from about 20 mole % to about 40 mole % of aliphatic dicarboxylic acid or ester thereof, from about 30 mole % to about 60 mole % dihydric alcohol, and wherein the weight average molecular weight of the copolyester is from about 90,000 to about 160,000 Daltons, and wherein the number average molecular weight of the copolyester is from about 35,000 to about 70,000 Daltons, and wherein the glass transition temperature of the copolyester is less than about 0° C., wherein the filler particles are coated up to 2% by weight with a fatty acid, and wherein the fatty acid is behenic acid.

2. The absorbent article as set forth in claim 1 wherein the filler particles are present in the film in an amount of from about 30% (by weight of film and filler particles) to about 80% (by weight of film and filler particles).

3. The absorbent article as set forth in claim 1 wherein the filler particles are present in the film in an amount of from about 50% (by weight of film and filler particles) to about 55% (by weight of film and filler particles).

4. The absorbent article as set forth in claim 1 wherein the filler particles are selected from the group consisting of calcium carbonate, non-swellable clays, silica, alumina, barium sulfate, sodium carbonate, talc, magnesium sulfate, titanium dioxide, zeolites, aluminum sulfate, diatomaceous earth, magnesium sulfate, magnesium carbonate, barium carbonate, kaolin, mica, carbon, calcium oxide, magnesium oxide, aluminum hydroxide and polymer particles.

5. The absorbent article as set forth in claim 4 wherein the filler particles are calcium carbonate.

6. The absorbent article as set forth in claim 1 wherein the filler particles are nonporous.

7. The absorbent article as set forth in claim 1 wherein the copolyester comprises from about 15 mole % to about 25 mole % of aromatic dicarboxylic acid or ester thereof, from about 25 mole % to about 35% percent of aliphatic dicarboxylic acid or ester thereof, and from about 45 mole % to about 55 mole % dihydric alcohol and wherein the weight average molecular weight of the copolyester is from about 100,000 to about 130,000 Daltons, and wherein the number average molecular weight of the copolyester is from about 40,000 to about 60,000 Daltons.

8. The absorbent article as set forth in claim 1 wherein the copolyester comprises from about 17.5 mole % to about 22.5 mole % of aromatic dicarboxylic acid or ester thereof, from about 27.5 mole % to about 32.5 mole % percent of aliphatic dicarboxylic acid or ester thereof, and from about 47.5 mole % to about 52.5 mole % dihydric alcohol and wherein the weight average molecular weight of the copolyester is from about 105,000 to about 120,000 Daltons, and wherein the number average molecular weight of the copolyester is from about 42,000 to about 50,000 Daltons.

9. The absorbent article as set forth in claim 1 wherein the aromatic dicarboxylic acid or ester thereof is selected from the group consisting of unsubstituted and substituted aromatic dicarboxylic acids and $C_1$-$C_6$ esters of aromatic dicarboxylic acids.

10. The absorbent article as set forth in claim 1 wherein the aromatic dicarboxylic acid or ester thereof is selected from the group consisting of terephthalic acid, dimethyl terephthalate, isophthalic acid, dimethyl isophthalate, 2,6-napthalene dicarboxylic acid, dimethyl-2,6-naphthalate, 2,7 -naphthalenedicarboxylic acid, dimethyl-2,7-naphthalate, 3,4'-diphenyl ether dicarboxylic acid, dimethyl-3,4'diphenyl ether dicarboxylate, 4,4'-diphenyl ether dicarboxylic acid, dimethyl-4,4'-diphenyl ether dicarboxylate, 3,4'-diphenyl sulfide dicarboxylic acid, dimethyl-3,4'-diphenyl sulfide dicarboxylate, 4,4'-diphenyl sulfide dicarboxylic acid, dimethyl-4,4'-diphenyl sulfide dicarboxylate, 3,4'-diphenyl sulfone dicarboxylic acid, dimethyl-3,4'-diphenyl sulfone dicarboxylate, 4,4'-diphenyl sulfone dicarboxylic acid, dimethyl-4,4'-diphenyl sulfone dicarboxylate, 3,4'-benzophenonedicarboxylic acid, dimethyl-3,4'-benzophenonedicarboxylate, 4,4'-benzophenonedicarboxylic acid, dimethyl-4,4'-benzophenonedicarboxylate, 1,4-naphthalene dicarboxylic acid, dimethyl-1,4-naphthalate, 4,4'-methylene bis(benzoic acid), dimethyl-4,4'-methylenebis(benzoate), and mixtures of two or more thereof.

11. The absorbent article as set forth in claim 1 wherein the aliphatic dicarboxylic acid or ester thereof is selected from the group consisting of oxalic acid, dimethyl oxalate, malonic acid, dimethyl malonate, succinic acid, dimethyl succinate, methylsuccinc acid, glutaric acid, dimethyl glutarate, 2-methylglutaric acid, 3-methylglutaric acid, adipic acid, dimethyl adipate, 3-methyladipic acid, 2,2,5,5-tetramethylhexanedioic acid, pimelic acid, suberic acid, azelaic acid, dimethyl azelate, sebacic acid, 1,11-undecanedicarboxylic acid, 1,10-decanedioic acid, undecanedioic acid, 1,12-dodecanedicarboxylic acid, hexadecanedioic acid, docosanedioic acid, tetracosanedioic acid, dimer acid, 1,4-cyclohexanedicarboxylic acid, dimethyl-1,4-cyclohexanedicarboxylate, 1,3-cyclohexanedicarboxylic acid, dimethyl-1,3-cyclohexanedicarboxylate, 1,1-cyclohexanediacetic acid, and mixtures of two or more thereof.

12. The absorbent article as set forth in claim 1 wherein the aliphatic dicarboxylic acid or ester thereof is selected from the group consisting of succinic acid, dimethyl succinate, glutaric acid, dimethyl glutarate, adipic acid, dimethyl adipate, and dimer acid.

13. The absorbent article as set forth in claim 1 wherein the dihydric alcohol is selected from the group consisting of unsubstituted or substituted, straight chain, branched, or cyclic aliphatic, aliphatic-aromatic, or aromatic diols having from 2 carbon atoms to 36 carbon atoms and poly(alkylene ether) glycols with molecular weights from about 250 to about 4,000.

14. The absorbent article as set forth in claim 1 wherein the dihydric alcohol is selected from the group consisting of ethylene glycol, 1,3-propanediol, 1,4-butanediol, 1,6-hexanediol, 1,8-octanediol, 1,10-decanediol, 1,12-dodecanediol, 1,14-tetradecanediol, 1,16-hexadecanediol, 4,8-bis(hydroxymethyl)-tricyclo[5.2.1 .0/2.6]decane, 1,4-cyclohexanedimethanol, di(ethylene glycol), tri(ethylene glycol), poly(ethylene oxide) glycols, poly(butylene ether) glycols, isosorbide, and mixtures of two or more thereof.

15. The absorbent article as set forth in claim 1 wherein the dihydric alcohol is selected from the group consisting of ethylene glycol, 1,3-propanediol, 1,4-butanediol, 1,6-hexanediol, and poly(ethylene oxide) glycols.

16. The absorbent article as set forth in claim 1 wherein the polyfunctional branching agent is selected from the group consisting of a material with three or more carboxylic acid functions, three or more hydroxy functions, and mixtures thereof.

17. The absorbent article as set forth in claim 1 wherein the polyfunctional branching agent is selected from the group consisting of 1,2,4-benzenetricarboxylic acid (trimellitic acid), trimethyl-1,2,4-benzenetricarboxylate, 1,2,4-benzenetricarboxylic anhydride (trimellitic anhydride), 1,3,5-benzenetricarboxylic acid, 1,2,4,5-benzenetetracarboxylic acid (pyromellitic acid), 1,2,4,5-benzenetetracarboxylic dianhydride (pyromellitic anhydride), 3,3',4,4'-benzophenonetetracarboxylic dianhydride, 1,4,5,8-naphthalenetetracarboxylic dianhydride, citric acid, tetrahydrofuran-2,3,4,5-tetracarboxylic acid, 1,3,5-cyclohexanetricarboxylic acid, pentaerythritol, 2-(hydroxymethyl)-1,3-propanediol, 2,2-bis(hydroxymethyl)propionic acid, and mixtures of two or more thereof.

18. The absorbent article as set forth in claim 1 wherein the aromatic dicarboxylic acid is terephthalic acid, the aliphatic dicarboxylic acid is adipic acid, and the dihydric alcohol is 1,4 butanediol.

19. The absorbent article as set forth in claim 18 wherein the filler material is calcium carbonate.

20. The absorbent article as set forth in claim 1 wherein the film has a thickness of less than about 250 micrometers.

21. The absorbent article as set forth in claim 1 wherein the film has a thickness of from about 2.5 micrometers to about 130 micrometers.

22. The absorbent article as set forth in claim 1 wherein the laminated outercover further comprises a nonwoven material.

23. The absorbent article as set forth in claim 22 wherein the nonwoven material is a spunbonded nonwoven material.

24. The absorbent article as set forth in claim 22 wherein the nonwoven material has a basis weight of less than about 30 grams per square meter.

25. The absorbent article as set forth in claim 22 wherein the film and the nonwoven material are bonded together with an adhesive.

26. The absorbent article as set forth in claim 22 wherein the film and the nonwoven material are thermally bonded together.

27. The absorbent article as set forth in claim 22 wherein the film and the nonwoven material are ultrasonically bonded together.

28. The absorbent article as set forth in claim 1 wherein the laminated outercover further comprises a bonded carded web.

29. The absorbent article as set forth in claim 1 wherein the laminated outercover further comprises a spunbond-meltblown laminate.

30. The absorbent article as set forth in claim 1 wherein the laminated outercover further comprises a spunlace nonwoven.

31. The absorbent article as set forth in claim 1 wherein the laminated outercover further comprises a polylactic acid-based substrate.

32. The absorbent article as set forth in claim 1 wherein the film has a hydrostatic pressure resistance of at least about 60 millibar.

33. The absorbent article as set forth in claim 1 wherein the film has a hydrostatic pressure resistance of at least about 80 millibar.

34. The absorbent article as set forth in claim 1 wherein the film has a hydrostatic pressure resistance of at least about 120 millibar.

35. The absorbent article as set forth in claim 1 wherein the film has a hydrostatic pressure resistance of at least about 180 millibar.

36. The absorbent article as set forth in claim 1 wherein the film has a water vapor transmission rate of at least about 2000 g/m²/day.

37. The absorbent article as set forth in claim 1 wherein the film has a water vapor transmission rate of at least about 5,000 g/m²/day.

38. The absorbent article as set forth in claim 1 wherein the film has a water vapor transmission rate of at least about 10,000 g/m²/day.

39. The absorbent article as set forth in claim 1 wherein the film has a water vapor transmission rate of at least about 25,000 g/m²/day.

40. The absorbent article as set forth in claim 1 wherein the film has a modulus of elasticity of from about 50 MPa to about 250 MPa.

41. The absorbent article as set forth in claim 1 wherein the film has a modulus of elasticity of from about 70 MPa to about 150 MPa.

42. The absorbent article as set forth in claim 1 wherein the film has a modulus of elasticity of from about 80 MPa to about 100 MPa.

43. The absorbent article as set forth in claim 1 wherein the film can be stretched in the machine direction and not break until from about 15% strain to about 100% strain is reached.

44. The absorbent article as set forth in claim 1 wherein the film can be stretched in the machine direction and not break until from about 20% strain to about 60% strain is reached.

45. The absorbent article as set forth in claim 1 wherein the film can be stretched in the machine direction and not break until from about 30% strain to about 50% strain is reached.

46. The absorbent article as set forth in claim 1 wherein the film can be stretched in the cross direction and not break until from about 150% strain to about 500% strain is reached.

47. The absorbent article as set forth in claim 1 wherein the film can be stretched in the cross direction and not break until from about 175% strain to about 400% strain is reached.

48. The absorbent article as set forth in claim 1 wherein the film can be stretched in the cross direction and not break until from about 200% strain to about 300% strain is reached.

49. The absorbent article as set forth in claim 1 wherein the film has a break stress of from about 10 MPa to about 50 MPa.

50. The absorbent article as set forth in claim 1 wherein the film has a break stress of from about 15 MPa to about 40 MPa.

51. The absorbent article as set forth in claim 1 wherein the film has a break stress of from about 25 MPa to about 35 MPa.

52. The absorbent article as set forth in claim 1 wherein the absorbent article is selected from the group consisting of diapers, training pants, and adult incontinence garments.

53. An absorbent article comprising a laminated outer cover, the laminated outer cover comprising a biodegradable stretched aliphatic-aromatic copolyester film, the film comprising filler particles, a polyfunctional branching agent, and a copolyester comprising from about 10 mole % to about 30 mole % terephthalic acid, from about 20 mole % to about 40 mole % adipic acid, from about 30 mole % to about 60 mole % 1,4-butanediol, and wherein the copolyester has a weight average molecular weight of from about 90,000 to about 160,000 Daltons and a number average molecular weight of from about 35,000 to about 70,000 Daltons, and wherein the glass transition temperature of the copolyester is less that about 0° C., wherein the filler particles are coated up to 2% by weight with a fatty acid, and wherein the fatty acid is behenic acid.

54. The absorbent article as set forth in claim 53 wherein the filler particles are present in the film in an amount of from about 30% (by weight of film and filler particles) to about 80% (by weight of film and filler particles).

55. The absorbent article as set forth in claim 53 wherein the filler particles are selected from the group consisting of calcium carbonate, non-swellable clays, silica, alumina, barium sulfate, sodium carbonate, talc, magnesium sulfate, titanium dioxide, zeolites, aluminum sulfate, diatomaceous earth, magnesium sulfate, magnesium carbonate, barium carbonate, kaolin, mica, carbon, calcium oxide, magnesium oxide, aluminum hydroxide and polymer particles.

56. The absorbent article as set forth in claim 55 wherein the filler particles are calcium carbonate.

* * * * *

UNITED STATES PATENT AND TRADEMARK OFFICE
CERTIFICATE OF CORRECTION

| | |
|---|---|
| PATENT NO. | : 7,776,020 B2 |
| APPLICATION NO. | : 10/804921 |
| DATED | : August 17, 2010 |
| INVENTOR(S) | : Ross Thomas Kaufman et al. |

It is certified that error appears in the above-identified patent and that said Letters Patent is hereby corrected as shown below:

In the Specification

In Column 6, Line 26, delete "11,2,4" and insert -- 1,2,4 -- therefor.

In Table 7, Column 15, Line 44, delete "15.660" and insert -- 15,660 -- therefor.

Signed and Sealed this
Twelfth Day of May, 2015

Michelle K. Lee
*Director of the United States Patent and Trademark Office*